(12) United States Patent
Rubin et al.

(10) Patent No.: US 7,154,987 B2
(45) Date of Patent: Dec. 26, 2006

(54) PROJECTION GATING OF X-RAY CT SCAN

(75) Inventors: Jonathan M. Rubin, Ann Arbor, MI (US); Benoit Desjardins, Ann Arbor, MI (US); J. Brian Fowlkes, Ann Arbor, MI (US); Srini Tridandapani, Saline, MI (US)

(73) Assignee: The Regents of the University of Michigan, Ann Arbor, MI (US)

( * ) Notice: Subject to any disclaimer, the term of this patent is extended or adjusted under 35 U.S.C. 154(b) by 0 days.

(21) Appl. No.: 11/222,105

(22) Filed: Sep. 8, 2005

(65) Prior Publication Data
US 2006/0056578 A1 Mar. 16, 2006

Related U.S. Application Data

(60) Provisional application No. 60/608,333, filed on Sep. 9, 2004.

(51) Int. Cl.
*G01N 23/083* (2006.01)
(52) U.S. Cl. .............................. 378/8; 378/4
(58) Field of Classification Search .............. 378/4–20, 378/95, 901; 600/427, 428, 509, 522
See application file for complete search history.

(56) References Cited

U.S. PATENT DOCUMENTS

| | | | |
|---|---|---|---|
| 4,858,128 A | 8/1989 | Nowak | |
| 5,337,231 A | 8/1994 | Nowak et al. | |
| 5,671,263 A | 9/1997 | Ching-Ming | |
| 6,192,265 B1 | 2/2001 | Carlsen et al. | |
| 6,480,560 B1 | 11/2002 | Hsieh | |
| 6,522,712 B1 * | 2/2003 | Yavuz et al. | 378/4 |
| 2002/0025017 A1 | 2/2002 | Stergiopoulos et al. | |
| 2002/0118790 A1 | 8/2002 | Pan et al. | |
| 2002/0131545 A1 | 9/2002 | Hsieh | |
| 2003/0174804 A1 | 9/2003 | Bulkes et al. | |
| 2004/0125908 A1 * | 7/2004 | Cesmeli et al. | 378/4 |
| 2005/0238135 A1 * | 10/2005 | Younis et al. | 378/8 |

* cited by examiner

*Primary Examiner*—Edward J. Glick
*Assistant Examiner*—Anastasia S. Midkiff
(74) *Attorney, Agent, or Firm*—Quarles & Brady LLP

(57) ABSTRACT

An x-ray CT system performs a scan by acquiring projection views from which an image is reconstructed. In a prospective embodiment, the correlation of adjacent views is calculated as the scan is performed and is used to detect subject motion as the scan is being performed. In a retrospective embodiment, the correlation of adjacent views is calculated and is used to detect subject motion after the scan is completed. In the first embodiment substitute projection views are acquired by continuing the scan and in the second embodiment redundant projection views acquired during the scan are substituted until the best possible image is produced.

14 Claims, 4 Drawing Sheets

PROJECTION GATING OF X-RAY CT SCAN

CROSS-REFERENCE TO RELATED APPLICATIONS

This application claims the benefit of U.S. Provisional patent application Ser. No. 60/608,333 filed on Sep. 9, 2004 and entitled "Projection Gating Of X-Ray Scan".

BACKGROUND OF THE INVENTION

This invention relates generally to methods and apparatus for CT imaging and other radiation imaging systems and, more particularly, to a method for reducing image artifacts caused by subject motion.

In at least some "computed tomography" (CT) imaging system configurations, an x-ray source projects a fan-shaped beam which is collimated to lie within an X-Y plane of a Cartesian coordinate system, generally referred to as an "imaging plane". The x-ray beam passes through a subject being imaged, such as a patient. The beam, after being attenuated by the object, impinges upon an array of radiation detectors. The intensity of the attenuated radiation beam received at a detector array is dependent upon the attenuation of the x-ray beam by the object. Each detector element of the array produces a separate electrical signal that is a measurement of the beam attenuation at the detector location. The attenuation measurements from all the detectors are acquired separately to produce a transmission profile, or "projection".

In known third generation CT systems, the x-ray source and the detector array are rotated with a gantry within the imaging plane and around the object to be imaged, so the angle at which the x-ray beam intersects the object constantly changes. X-ray sources typically include x-ray tubes, which emit the x-ray beam at a focal spot. X-ray detectors typically include a collimator for collimating x-ray beams received at the detector, a scintillator adjacent the collimator, and photodetectors adjacent to the scintillator. A group of x-ray attenuation measurements, i.e., projection data, from the detector array at one gantry angle is referred to as a "view". A "scan" of the object comprises a set of views made at different gantry angles, or view angles, during one revolution of the x-ray source and detector.

In an axial scan, the projection data is processed to construct an image that corresponds to a two dimensional slice taken through the object. One method for reconstructing an image from a set of projection data is referred to in the art as the filtered back projection technique. This process converts the attenuation measurements from a scan into integers called "CT numbers" or "Hounsfield units," which are used to control the brightness of a corresponding pixel on a display.

To reduce the total scan time required for multiple slices, a "helical" scan may be performed. To perform a "helical" scan, the patient is moved in the z-axis synchronously with the rotation of the gantry, while the data for the prescribed number of slices is acquired. Such a system generates a single helix from a fan beam helical scan. The helix mapped out by the fan beam yields projection data from which images in each prescribed slice may be reconstructed.

When an image is acquired of the beating heart or surrounding tissues, it is difficult to produce an image without artifacts. The cardiac cycle includes a period of relaxation and dilation of the heart cavities known as diastole, and a period of contraction of the heart during which blood is ejected from the ventricles known as systole. A typical period of time for one cardiac cycle is slightly less than one second. Thus, a heart goes through a substantial portion of its cycle during one gantry revolution. Motion induced image artifacts result from such heart motion. Known cardiac CT scanners utilize "electro-cardio-gram" (ECG) signals to gate the acquisition of scan data. Typically, leads are connected to a patient to measure the ECG signal, which indirectly represents a cardiac cycle.

With ECG cardiac gating the presumption is made that there is a direct and consistent correlation between the phases of the ECG periodic signal and the physical position and shape of the heart. Thus, if data is acquired only during a particular phase or phases of the periodic ECG signal, the assumption is that the heart will be in a particular position and shape when all the scan data is acquired. This assumption is not always correct. For instance, the heart rate typically changes during the injection of contrast agents that are required for imaging the coronary arteries. This creates real problems for ECG gating in that the fractions of the QRS interval that might successfully produce consistent data for static/gated images before injection would not be the same after contrast injection. There is no reason to believe that a given fraction of the ECG cycle would produce consistent reconstructions when the heart beat changes. At a minimum, more radiation will be required when the heart rate changes to acquire enough projections to permit adequate reconstructions. The situation is worse with arrhythmias. Depending on the arrhythmia, there may never be segments that are consistent from one ECG cycle to the next.

SUMMARY OF THE INVENTION

The present invention is a method for detecting x-ray projection views that are acquired at the same subject position and using that method to acquire complete sets of projection views from which an artifact-free image can be reconstructed. More particularly, as projection views are acquired during a CT scan, the correlation of a projection view and the projection view acquired at an adjacent view angle is calculated. A high correlation coefficient indicates the view was acquired at the same subject position as the adjacent view, whereas a dip in the correlation coefficient indicates motion has occurred. Once a desired subject reference position is established (e.g., a particular cardiac phase) projection views are acquired over the entire range of view angles and the correlation coefficients are checked to insure that the subject is captured in the same position in all views. A dip in the correlation coefficient of any projection view indicates that a substitute view should be acquired.

A general object of the invention is to improve x-ray CT images acquired from a moving subject such as a beating heart. ECG cardiac gating can be used to acquire views at or near the desired reference position and the correlation of each acquired view with an adjacent view is used to determine which view angles have been properly acquired and those that must be reacquired.

GENERAL DESCRIPTION OF THE INVENTION

The present invention is implemented on the projection data produced by a CT system. More specifically, as the projections (p) are acquired, the correlation of that projection and other acquired projections is calculated. For projections $p_j$ and $p_k$ acquired at adjacent view angles this correlation coefficient should be very close to 1 if no subject motion has occurred:

$$\rho(p_j, p_k) = \frac{\sum_{i=l_1}^{n_2}(X(i, p_j) - \overline{X}(p_j))(X(i, p_k) - \overline{X}(p_k))}{\sigma_{p_j}\sigma_{p_k}} \quad (1)$$

where $\rho$ is the correlation coefficient, $p_j$ is the jth x-ray projection set, $X(i,p_j)$ is the voltage value at the ith detector on the jth projection set, $\overline{X}(p_j)$ is the mean value for the jth projection set, and $\sigma_{p_j}$ is the standard deviation of the jth projection set. This correlation can be performed across all projection views. Projection views that are immediate neighbors such that k=j+1 for instance, should be very highly correlated. The detectors will have rotated only a few degrees. There is considerable overlap in the detector signals from adjacent views with the outside elements of the detector arrays being the only ones that detect any real differences. Thus, this sum can be taken from only the inner portions of the array, and these may be perfectly correlated, i.e., almost 1. This sum looks like equation (1) except $$\rho(p_j, p_k) = \frac{\sum_{i=1+\varepsilon_1}^{n-\varepsilon_2}(X(i, p_j) - \overline{X}(p_j))(X(i, p_k) - \overline{X}(p_k))}{\sigma_{p_j}\sigma_{p_k}} \quad (2)$$

where $\varepsilon$ is the number of detectors that do not overlap between neighboring projection views. In this case k=j+1 as stated above. This is analogous to a standard correlation of lag $\varepsilon$.

Figure 3:
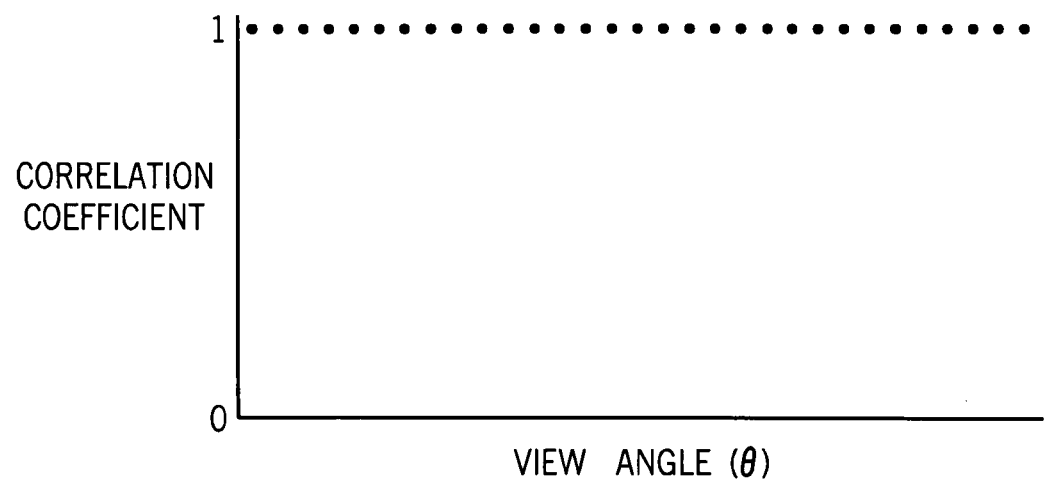
FIG. 3 is a graph illustrating the high correlation between successive projections acquired with the CT system of FIG. 1.
Figure 4:
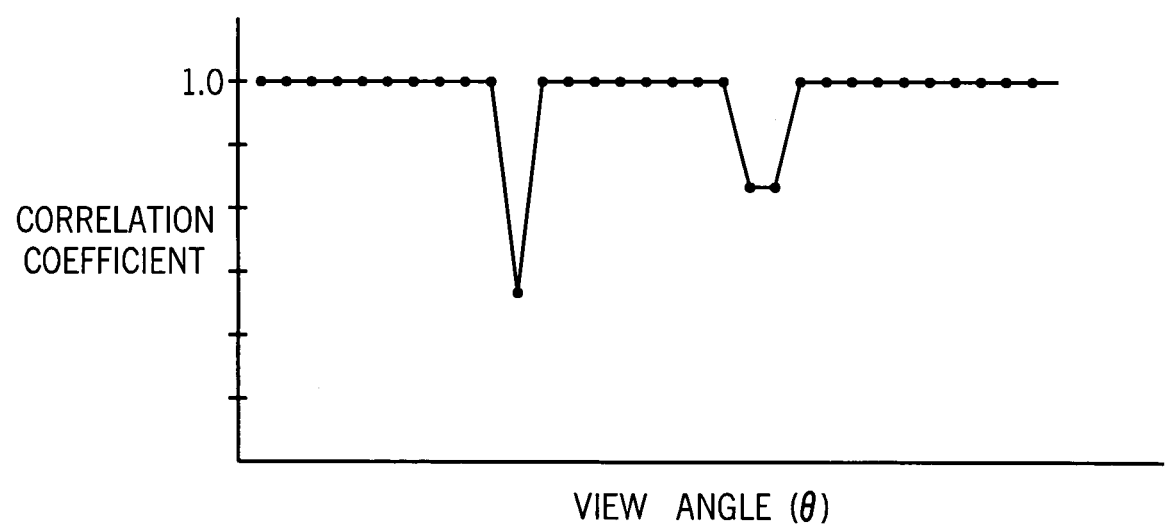
FIG. 4 is a graph illustrating a drop in correlation when subject motion occurs during the scan.

Using this method for detecting subject movement, a complete set of projection views can be acquired that depict the subject in a reference position. Referring to FIG. 3, a plot of the calculated correlation coefficients of such a set of projection views as a function of projection view angle will be a substantially straight line at or near the value 1. On the other hand, if a dip occurs in this correlation plot as shown in FIG. 4, subject motion away from the reference position is indicated while acquiring one or more projection views. In such case the suspect projection views are discarded and replacement views are acquired.

This detection method can be used either prospectively or retrospectively to acquire a motion free set of projection views. In a prospective implementation the correlation coefficients of adjacent views are calculated as the projection views are acquired, and the resulting correlation plot is examined to determine which projection views need to be replaced. The scan continues until the necessary number of replacement views are acquired. This is detected when the correlation plot is smoothed to a preselected level.

In a retrospective implementation redundant projection views are acquired and the correlation coefficients of an initial set of projection views is calculated after the scan is completed. The resulting correlation plot is examined to determine which projection views might be replaced to improve the smoothness of the plot, and a search is made among the redundant acquired projection views. The search is conducted by calculating the correlation coefficient for the candidate replacement view and the projection view adjacent the view to be replaced. If the correlation coefficient is higher, the replacement is made. This retrospective search for replacement projection views continues until all candidate replacement projection views have been evaluated or until the correlation plot reaches a predetermined level of smoothness.

DETAILED DESCRIPTION OF THE PREFERRED EMBODIMENT

Figure 1:
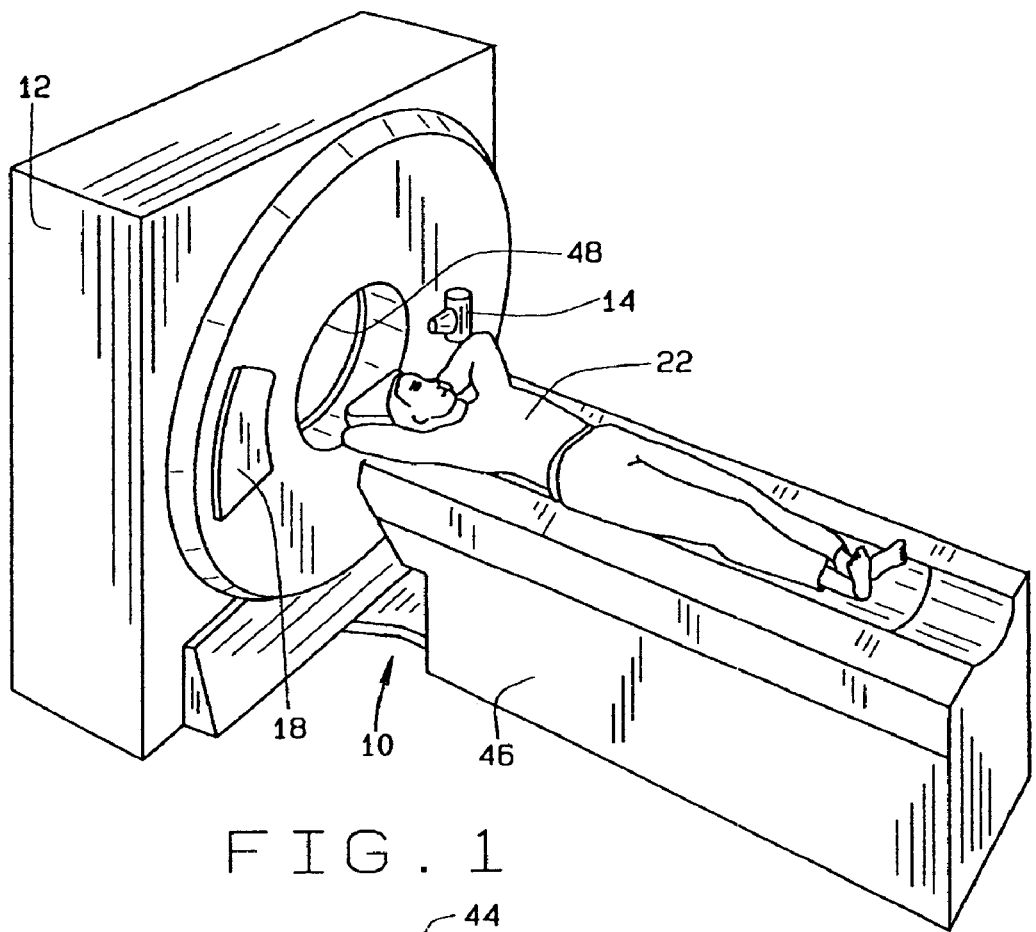
FIG. 1 is a perspective view of an x-ray CT system when employs the present invention.
Figure 2:
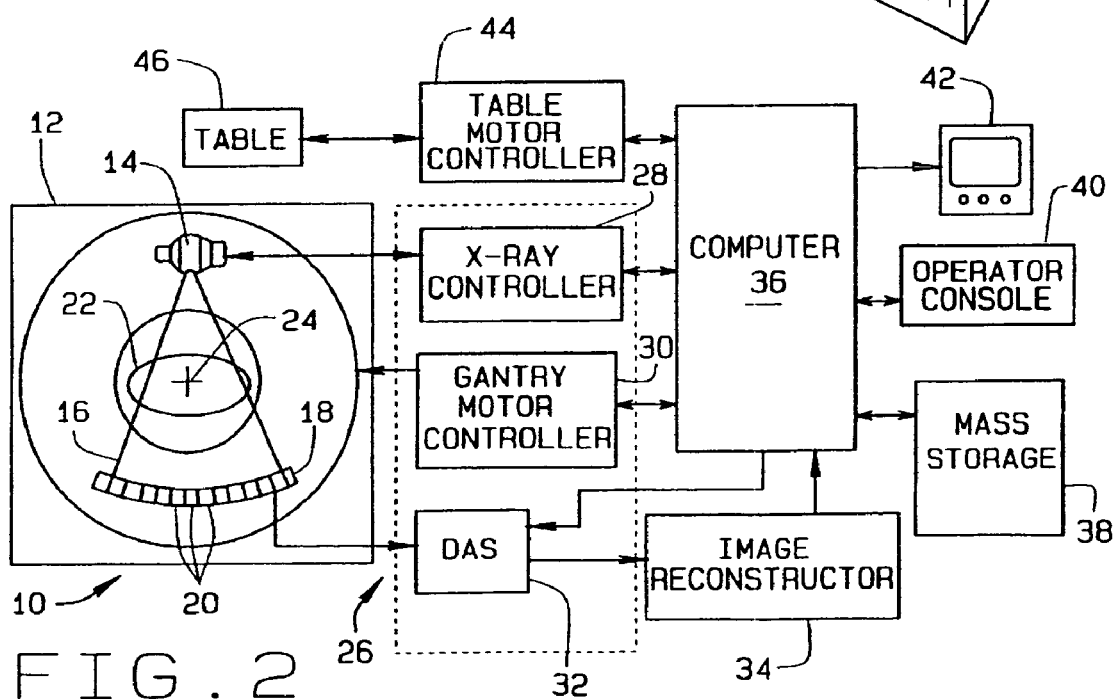
FIG. 2 is an electrical block diagram of the CT system of FIG. 1.

Referring to FIGS. 1 and 2, a computed tomography (CT) imaging system 10 is shown as including a gantry 12 representative of a "third generation" CT scanner. Gantry 12 has an x-ray source 14 that projects a beam of x-rays 16 toward a detector array 18 on the opposite side of gantry 12. Detector array 18 is formed by detector elements 20 which together sense the projected x-rays that pass through an object, such as a medical patient 22. Each detector element 20 produces an electrical signal that represents the intensity of an impinging x-ray beam and hence the attenuation of the beam as it passes through object or patient 22. During a scan to acquire x-ray projection data, gantry 12 and the components mounted thereon rotate about a center of rotation 24. In one embodiment, and as shown in FIG. 2, detector elements 20 are arranged in one row so that projection data corresponding to a single image slice is acquired during a scan. In another embodiment, detector elements 20 are arranged in a plurality of parallel rows, so that projection data corresponding to a plurality of parallel slices can be acquired simultaneously during a scan.

Rotation of gantry 12 and the operation of x-ray source 14 are governed by a control mechanism 26 of CT system 10. Control mechanism 26 includes an x-ray controller 28 that provides power and timing signals to x-ray source 14 and a gantry motor controller 30 that controls the rotational speed and position of gantry 12. A data acquisition system (DAS) 32 in control mechanism 26 samples analog data from detector elements 20 and converts the data to digital signals for subsequent processing. An image reconstructor 34 receives sampled and digitized x-ray data from DAS 32 and performs high speed image reconstruction. The reconstructed image is applied as an input to a computer 36 which stores the image in a mass storage device 38.

Computer 36 also receives commands and scanning parameters from an operator via console 40 that has a keyboard. An associated display 42 allows the operator to observe the reconstructed image and other data from computer 36. The operator supplied commands and parameters are used by computer 36 to provide control signals and information to DAS 32, x-ray controller 28 and gantry motor controller 30. In addition, computer 36 operates a table motor controller 44 which controls a motorized table 46 to position patient 22 in gantry 12. Particularly, table 46 moves portions of patient 22 through gantry opening 48.

Figure 5:
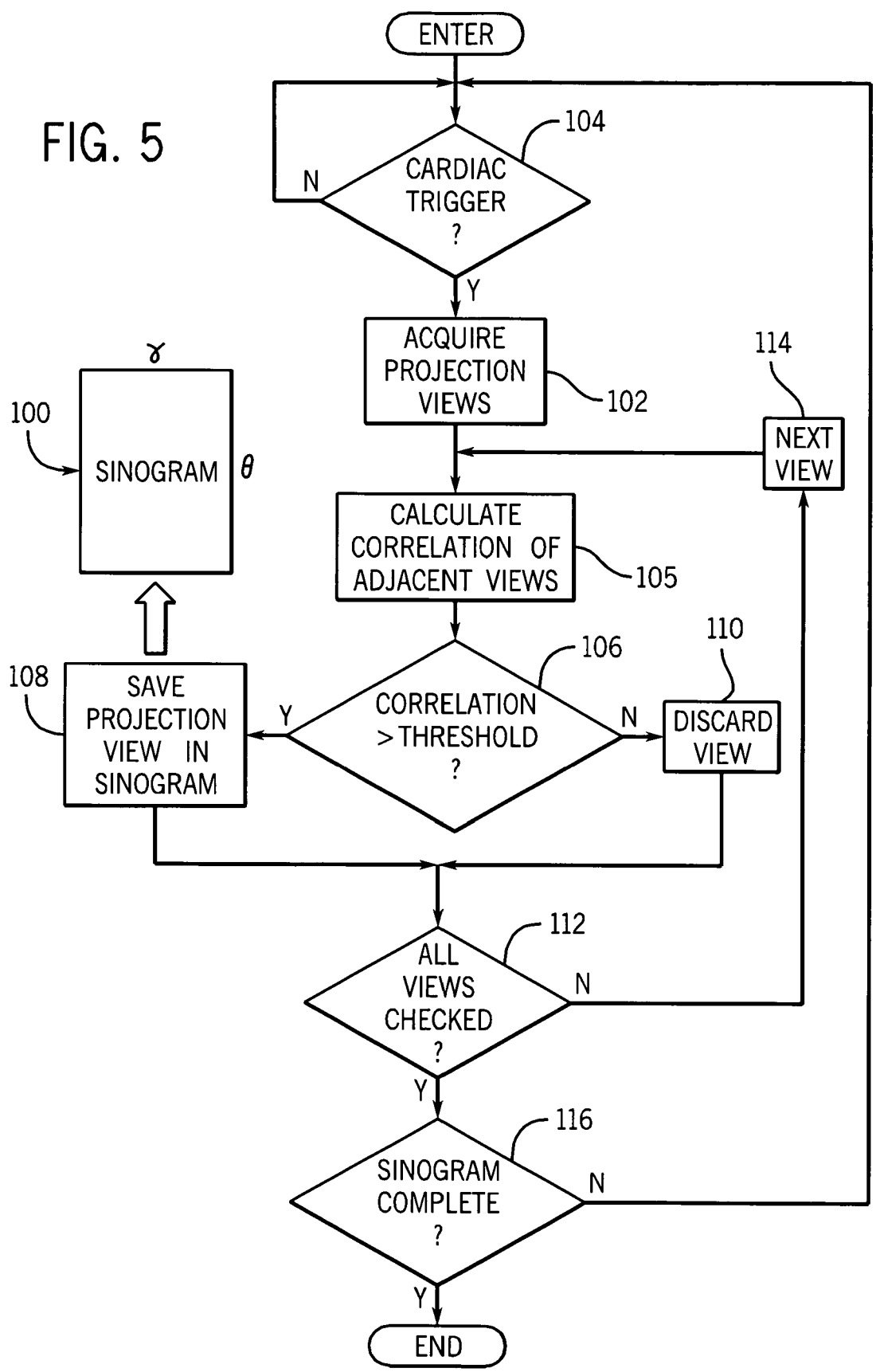
FIG. 5 is a flow chart of a first, prospective embodiment of the invention.

Referring particularly to FIG. 5, the present invention is embodied in a "prospective" motion detection application in which the scan continues until a good set of projection views from which the prescribed image can be reconstructed is acquired. Such a set of projection views are stored in a sinogram 100 as a function of the view angle θ at which they are acquired. Those skilled in the art will appreciate that while a single 2D sinogram is described herein, the scan prescription may call for the acquisition of multiple 2D slices or a 3D volume, in which case multiple 2D sinograms or a 3D sinogram may be acquired during the scan. According to this first embodiment, after the scan is complete the prescribed image or images can be reconstructed directly from the acquired sinogram(s).

Referring particularly to FIG. 5, the first embodiment is also a cardiac gated scan and views are acquired as indicated at process block 102 after receipt of an ECG cardiac trigger signal as detected at decision block 105. Depending on the cardiac phase at which the image is to be acquired, more than 1 projection view may be acquired after each trigger signal is received. As indicated at process block 104, the correlation of adjacent acquired projection views is then calculated using the above equation (1) or (2). If the correlation of a subject projection view and the prior acquired projection view at the adjacent view angle exceeds a preset threshold value as determined at decision block 106, the subject projection view is saved in the sinogram 100 as indicated at process block 108. If the subject projection view does not meet the correlation threshold, patient motion is presumed and the view is discarded as indicated at process block 110.

As indicated at decision block 112, a check is then made to determine if all the acquired projection views have been tested for motion. If not, the system loops back to test the next projection view as indicated at process block 114. Otherwise, the sinogram 100 is examined as indicated at decision block 116 to determine if a complete sinogram 100 has been acquired. If not, the system loops back to await the next cardiac trigger signal and the scan continues. If the sinogram 100 contains a complete set of projection views (as determined by the scan prescription), the data acquisition phase of the scan ends and the prescribed image is reconstructed from the acquired sinogram 100 using a filtered backprojection technique. It can be appreciated that the length of the data acquisition phase of the scan is indeterminant in this embodiment since data will continue to be acquired until the sinogram 100 is successfully filled.

Figure 6:
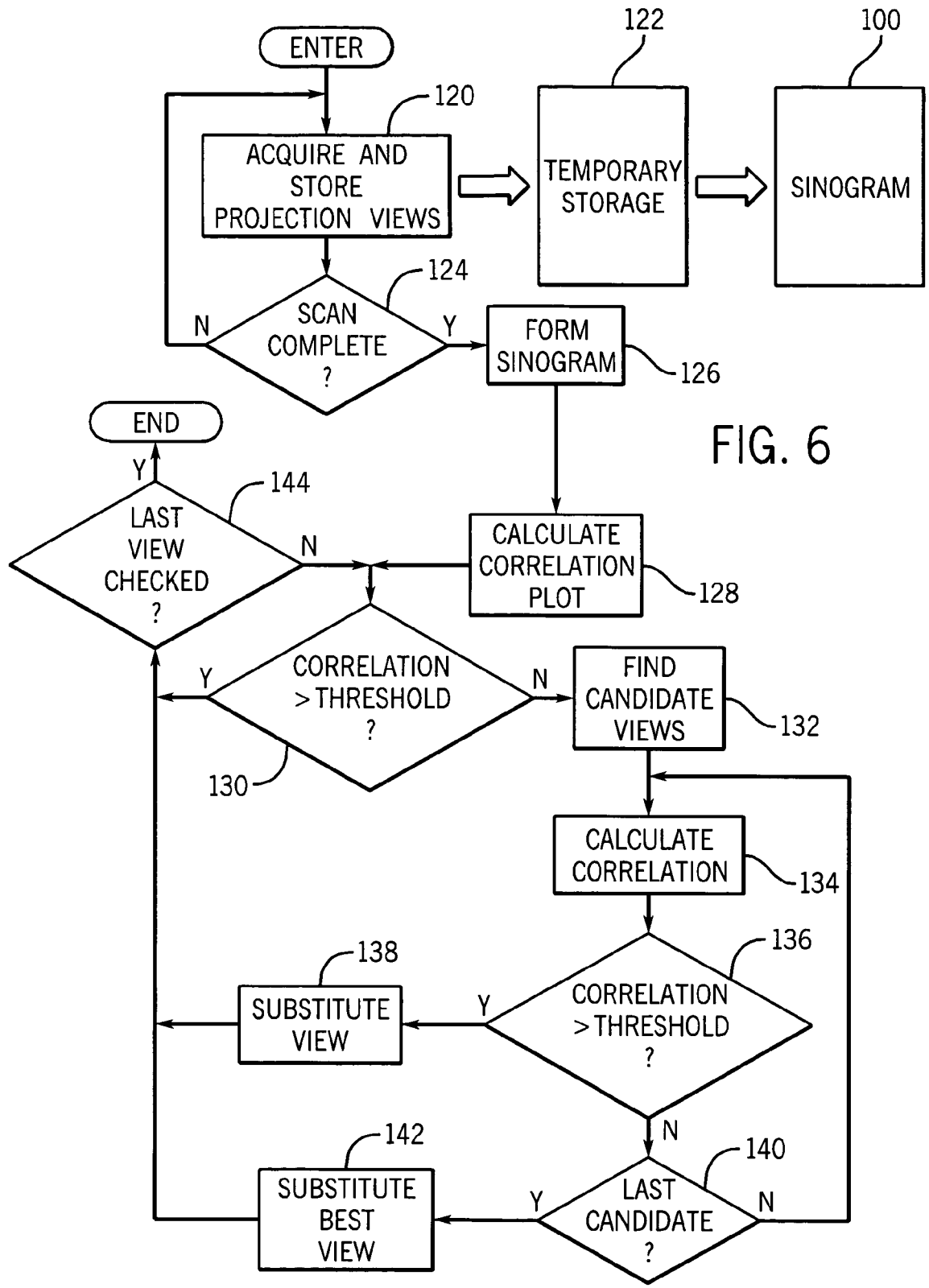
FIG. 6 is a flow chart of a second, retrospective embodiment of the invention.

Referring particularly to FIG. 6, the present invention is also embodied in a "retrospective" motion detection application in which a scan is performed and the best possible set of projection views are selected from the acquired data to form the sinogram from which the prescribed image is reconstructed. As with the first embodiment, although a single 2D image slice is described, the second embodiment may acquire a plurality of 2D slice images or a 3D image.

In the retrospective embodiment all of the projection views are acquired prior to examination for patient motion. Views are acquired as indicated at process block 120 and all of them are saved in temporary storage 122. When the scan is complete as determined at decision block 124, the data acquisition phase of the scan is completed. In this embodiment of the invention the length of the data acquisition phase of the scan is set to a known value, but it is designed to acquire redundant projection views. For example, in a 2D single slice scan, rather than a single gantry revolution, data may be acquired over a plurality of gantry revolutions. All of this data is saved in temporary storage 122, and for any given view angle, there will be a corresponding plurality of projection views to choose from.

After the acquisition phase is completed projection views are selected from the temporary storage 122 to form a complete sinogram 100 as indicated at process block 126. In this preferred embodiment successive projection views from the first gantry rotation are selected for this initial sinogram. A correlation plot is then calculated as indicated at process block 128. As described above, this is the calculation of the correlation of each successive view in the sinogram 100 with the adjacent view acquired immediately after using either equation (1) or (2).

A loop is then entered in which the correlation values in the correlation plot are successively tested to detect corrupted projection views and replace them. More specifically, if the correlation value of a subject projection view is not above a preselected threshold as indicated at decision block 130, a search is made as indicated by process block 132 for a candidate substitute projection view in temporary storage 122. As indicated above, when this retrospective embodiment is used redundant projection views are acquired during the scan and one or more projection views at the same view angle θ and slice location can be found as candidate substitute views.

The candidate substitute views are then checked to determine the best possible substitute. As indicated at process block 134, the correlation of the candidate substitute with the adjacent projection view is calculated and if the correlation exceeds the preset threshold as determined at decision block 136, the substitute is made as indicated at process block 138. If the candidate does not meet the correlation threshold, the system loops back to check any additional candidate projection views at decision block 140. If all the candidates fail to meet the correlation threshold as determined at decision block 140, the best projection view is substituted in the sinogram 100 as indicated at process block 142. The best projection view is that one which yields the highest correlation coefficient.

When none of the candidate views meets the correlation threshold, a preferred approach is to motion correct the view that produces the highest correlation value. Numerous methods for motion correction are known in the art, but in the preferred embodiment the candidate view is shifted left or right in position until the correlation between it and the adjacent view is maximized.

The successive views are examined as described above until all of the views in the correlation plot have been examined as determined at decision block 144. The best possible sinogram 100 results from this process and an image is reconstructed from the sinogram 100 using a conventional filtered backprojection technique.

It should be apparent to those skilled in the art that variations can be made in the preferred embodiment described above without departing from the spirit of the invention. For example, the retrospective embodiment described above with reference to FIG. 6 can be modified to acquire cardiac phase information concurrently with the acquisition of projection views in process step 120. That is, the time interval after receipt of each ECG trigger signal is recorded with each acquired projection view. When the initial sinogram is formed at process step 126, projection views acquired at a particular cardiac cycle phase can therefore be chosen to form the image. For example, ejection fraction or wall motion images may be desired during the systole portion of the cardiac cycle when heart motion is at its peak. The present invention enables the best possible views to be selected from the acquired data in temporary storage 122 to produce an image at such a selected cardiac phase.

The invention claimed is:

1. A method for producing an image of a subject with projection views acquired by a medical imaging system, the steps comprising:
   a) forming a sinogram by acquiring projection views with the medical imaging system, the sinogram including a set of projection views acquired at a succession of view angles;
   b) calculating the correlation of adjacent projection views in the sinogram;
   c) correcting the sinogram by substituting other projection views acquired with the medical imaging system into the sinogram based on the calculated correlation of the substituted projection view and an adjacent projection view; and
   d) reconstructing the image from the corrected sinogram.

2. The method as recited in claim 1 in which steps a), b) and c) are performed while the subject is positioned in the medical imaging system.

3. The method as recited in claim 2 in which step a) is performed until step c) is completed.

4. The method as recited in claim 3 in which step a) includes producing a cardiac trigger indicating the subject's cardiac phase and acquiring the projection views at a selected cardiac phase.

5. The method as recited in claim 1 in which redundant projection views are acquired in step a) and step a) is completed before steps b), c) and d) are performed.

6. The method as recited in claim 5 in which step c) is performed by selecting a redundant projection view based on its calculated correlation.

7. The method as recited in claim 6 in which the selected projection view has a correlation which exceeds a preset threshold.

8. The method as recited in claim 6 in which the selected projection view has a highest correlation value.

9. The method as recited in claim 1 in which the medical imaging system is an x-ray computed tomography system and step a) is performed by rotating an x-ray source around the subject.

10. A method for producing an image of a subject with a medical imaging system, the steps comprising:
    a) acquiring projection views with the medical imaging system at a plurality of view angles;
    b) forming a sinogram by selecting from acquired projection views a set of projection views at successive view angles;
    c) correcting the sinogram by substituting other acquired projection views into the sinogram based on a calculation of the correlation of the substituted projection view and an adjacent projection view in the sinogram; and
    d) reconstructing the image from the corrected sinogram.

11. The method as recited in claim 10 in which step a) includes recording a cardiac phase of the subject as each projection view is acquired; and
    the sinogram is formed in step b) by selecting projection views acquired at a selected cardiac phase.

12. The method as recited in claim 11 in which step c) includes substituting a candidate projection view acquired at the selected cardiac phase which has the highest correlation with an adjacent view in the sinogram.

13. The method as recited in claim 10 in which step c) also includes motion correcting the substituted projection view.

14. The method as recited in claim 10 in which the medical imaging system is an x-ray computed tomography system and step a) is performed by rotating an x-ray source around the subject.

* * * * *